United States Patent [19]

Dawson et al.

[11] 4,027,036

[45] May 31, 1977

[54] 3-SUBSTITUTED PROPANOIC ACID DERIVATIVES AND PHARMACEUTICAL COMPOSITION

[75] Inventors: William Dawson, Camberley; Michael John Foulis, Binfield; Norman James Albert Gutteridge, Owlsmoor; Colin William Smith, Bracknell, all of England

[73] Assignee: Lilly Industries, Ltd., London, England

[22] Filed: Apr. 10, 1974

[21] Appl. No.: 459,829

[30] Foreign Application Priority Data

Apr. 12, 1973 United Kingdom ............. 17736/73

[52] U.S. Cl. .......................... 424/305; 260/468 K; 260/471 R; 260/473 P; 260/476 R; 260/487; 260/488 R; 260/514 K; 424/311

[51] Int. Cl.² ..................... A01N 9/24; C07C 61/38

[58] Field of Search ...... 260/468 K, 473 A, 488 R, 260/514 R, 520, 514 K, 487; 424/305, 311

[56] References Cited

UNITED STATES PATENTS

| | | | |
|---|---|---|---|
| 3,657,316 | 4/1972 | Samuelson | 260/471 R |
| 3,810,936 | 5/1974 | Miyano | 260/514 K X |

*Primary Examiner*—Anton H. Sutto
*Attorney, Agent, or Firm*—Steven R. Lammert; James L. Rowe; Everet F. Smith

[57] ABSTRACT

The invention provides 3-(2-formyl-3-hydroxy-5-oxocyclopent-1-enyl)-propanoic acid and derivatives thereof having anti-thrombotic activity coupled with low toxicity. Also provided is a method for preparing such compounds by subjecting a 3-[3-hydroxy-5-oxo-2-(β-styryl)cyclopent-1-enyl]-propanoic acid or derivative thereof to oxidative cleavage.

6 Claims, No Drawings

3-SUBSTITUTED PROPANOIC ACID DERIVATIVES AND PHARMACEUTICAL COMPOSITION

This invention relates to propanoic acid derivatives substituted in the 3-position by a cyclopentenyl group and to a method by which such compounds may be prepared. The novel compounds of this invention possess useful pharmacological activity and accordingly the present invention also provides pharmaceutical compositons comprising one or more of said novel compounds.

In the specification of our co-pending U.S. application Ser. No. 459,831 filed concurrently herewith, there are described inter alia compounds having the structure:

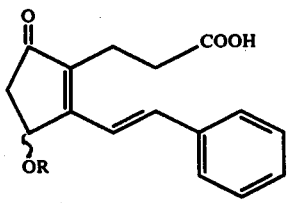

and salts and esters thereof, where R is hydrogen, acyl or benzoyl. As stated in the said specification, the foregoing compounds may exist in racemic or optically active form and are useful as spasmolytic agents.

It has now been discovered that, by removal of the styryl moiety from the above group of compounds, a further group of compounds may be obtained which also possess useful but different pharmacological activity.

According to the present invention therefore, there are provided compounds of the formula:

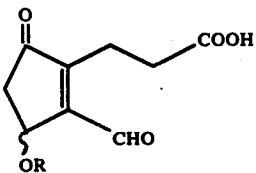

their enantiomorphs, and salts and esters thereof, wherein R is as defined above, and a process for the preparaton of said compound which comprises subjecting a compound of formula I, its enantiomorphs, or a salt or ester thereof to oxidative cleavage and thereafter optionally performing one or more of the following reactions:
  i. salifying or esterifying a resultant free acid of formula II;
  ii. acylating or benzoylating a resultant compound of formula II or a salt or ester thereof in which R is hydrogen;
  iii. resolving into its enantiomorphs a resultant racemic compound of formula II.

The salts of the acids of formula II are preferably alkali metal salts such as the sodium or potassium salts and, if these are prepared by optional step (i) above, that preparation may be readily accomplished by reaction of the acid with an appropriate base such as an alkali metal hydroxide, carbonate or hydrogen carbonate.

Examples of suitable esters of the acids of formula II include alkyl, silyl, cycloalkyl, cycloalkyl-alkyl, aralkyl, heteroaryl-alkyl, alkylaminoalkyl and alkoxyalkyl esters. Preferred esters are the $C_{1-4}$ alkyl esters optionally substituted by one or more halogen atoms such as the methyl, ethyl, n-propyl, isobutyl, t-butyl, chloromethyl, trifluoromethyl, 2-chloroethyl and 2,2,2-trichloroethyl esters. Where such esters are prepared by optional step (i) above, i.e. after the oxidative cleavage reaction, the preparation is carried out in conventional manner, for example by reacting the free acid of formula II with an appropriate alcohol in the presence of an acid catalyst. Thus the preferred esters of the invention may be prepared by reaction with, for example, methanol, ethanol, isopropanol, t-butanol, chloromethanol or 2,2,2-trichloroethanol in the presence of p-toluene sulphonic acid. The $C_{1-4}$ alkyl esters of the invention may also be prepared by reaction of the free acid with a diazoalkane such as diazomethane or diazoethane.

When R in formula II above is an acyl or benzoyl group, the preferred examples of such groups are $C_{2-4}$ acyl, $C_{2-4}$ -haloacyl, benzoyl, nitrobenzoyl, halobenzoyl, $C_{1-4}$ -alkylbenzoyl and $C_{1-4}$ alkoxybenzyl, and especially acetyl, propionyl, chloracetyl, 3,3,3-trichloropropionyl, benzoyl, p-nitrobenzoyl, p-chlorobenzyl, p-methylbenzoyl, and p-methoxybenzoyl. If R is hydrogen in the starting material of formula I and hence in the end product of formula II, the latter may readily be converted to a compound of formula II in which R is an acyl or benzoyl group by reaction with an appropriate acylating or benzoylating agent, for example an acyl or benzoyl halide, or an acid anhydride such as acetic anhydride, propionic anhydride, 3,3,3-trichloropropionic anhydride, acetyl chloride, benzoyl chloride, p-chlorobenzoyl chloride or p-nitrobenzoyl chloride.

The oxidative cleavage of the compounds of formula I to produce the desired compounds of formula II is conveniently carried out by treatment with osmium tetroxide and an alkali metal, such as potassium or sodium, periodate conveniently at room temperature. The tetroxide may be added in portions to the compound of formula I dissolved in a suitable solvent such as aqueous dioxan. The periodate is then added slowly and the reaction mixture is agitated for a few hours before being cooled to around 0° C. Any resultant precipitate is filtered off and the desired product is isolated from the filtrate.

As indicated above, the compounds of formula II are in racemic or optically active form depending on the form of the starting material of formula I. Where a racemate is obtained, it can be separated into its enantiomorphs in conventional manner, for example by chemical separation. The latter may be achieved by forming diastereoisomers from the racemic mixture by reaction with an appropriate optically active separating agent. Thus the free acids of formula II may be reacted with an optically active amine such as (−)-ephedrine or (+)- and (−)-α-methylbenzylamine, the difference in the solubility of the diastereoisomers obtained permitting selective recrystallisation of one form and regeneration of the optically active acids of formula II from the mixture.

As stated previously, the racemates and enantiomorphs of formula II, and their salts and esters, possess useful pharmacological activity, especially anti-thrombotic activity, coupled with low toxicity and may therefore be used in the treatment and inhibition of thrombosis in animals. This activity has been demonstrated at doses from about 1 to 150 mg./Kg. dependng on the test procedure used. In the treatment of humans, the effective dosage range will normaly lie between 5 and 25 mg./Kg. although other dosing schedules may be used at the discretion of the physician treating the patient.

The compounds of this invention also find a use in the prevention of platelet aggregation in stored blood. For this purpose, the active compound is added to the blood in amounts of from 10 to 1000 µg./ml., preferably 50 to 500 µg./ml.

In therapeutic use, the active compounds of the invention may be administered enterally, preferably orally, or parenterally, preferably intravenously and for this purpose they will normally be formulated into pharmaceutical compositions comprising the active ingredient in association with at least one pharmaceutically acceptable carrier therefor. Such compositions form a part of this invention and will normally consist of the active ingredient mixed with a carrier, or diluted by a carrier, or enclosed or encapsulated by a carrier in the form of a capsule, sachet, cachet or other container. The carrier may be a solid, semi-solid or liquid material which serves as a vehicle, excipient, coating agent, or medium for the active ingredient. Some examples of the carriers which may be used are lactose, dextrose, sucrose, sorbitol, mannitol, starch, gum acacia, calcium phosphate, liquid paraffin cocoa butter oil of theobroma, alginates, tragacanth, gelatin, methyl cellulose, polyoxyethylene sorbitan monolaurate, methyl- or propyl-hydroxybenzoate ethyl cellulose acetate phthalate, low viscosity acetyl cellulose acetate, paraffin wax, mineral wax, vegetable wax, vegetable gum, silicone rubbers such as liquid polydimethylsiloxane rubber, plasticised or unplasticised polyvinyl chloride, plasticised polyethylene teraphthalate, modified collagen, cross-linked hydrophilic polyether gel, cross-linked polyvinyl alcohol or cross-linked partially hydrolysed polyvinyl acetate.

Advantageously the compositions of the invention are formulated in a dosage unit form containing from 5 to 500 mg. (preferably 10 to 150 mg.) of the active ingredient. Examples of suitable dosage unit forms are tablets, hard or soft gelatin capsules, microcapsules and suppositories as well as drug dispensing systems comprising the active ingredient contained in a flexible, imperforate polymeric material through which the drug may be released slowly by diffusion. More generally, the term "dosage unit form" as used herein means a physicially discrete unit containing the active ingredient, generally in admixture with and/or enclosed by a pharmaceutical carrier, the quantity of active ingredient being such that one or more units are normally required for a single therapeutic administration.

The following Examples illustrate the preparation of the novel compounds of this invention

EXAMPLE 1

Aqueous osmium tetroxide solution (23 ml., 2%) was added dropwise to a solution of 3-[3-hydroxy-5-oxo-2-(β-styryl)cyclopent-1-enyl]propanoic acid (20 g.) in aqueous dioxan (750 ml., 80%) at room temperature. The mixture was stirred for 1/2 hour and sodium periodate (35 g.) was added in portions. After stirring for a further 2 hours at room temperature, the reaction mixture was cooled to 0° C. The precipitated solid was filtered off and the filtrate rotary evaporated to give a brown oil. The oil was dissolved in water, shaken well with ether, the aqueous phase was removed and evaporated to an oil which was then extracted with ethyl acetate. The organic extract was dried over anhydrous magnesium sulphate and rotary evaporated to an oil. Chromatography of the oil on a silicic acid column in 1% methanol/chloroform gave the desired 3-(2-formyl-3-hydroxy-5-oxocyclopent-1-enyl)propanoic acid as an oil, λmax (MeOH) 227 nm., εmax 7,600, mono phenyl hydrazone derivative, m.p. 175°–176° C.

EXAMPLE 2

By the method of Example 1 but using (+)- or (−)-3-[3-hydroxy-5-oxo-2-(β-styryl)cyclopent-1-enyl]-propanoic acid, there were obtained (+)-3-(2-formyl-3-hydroxy-5-oxocylopent-1-enyl)propanoic acid and (−)-3-(2-formyl-3-hydroxy-5-oxocyclopent-1-enyl)-propanoic acid respectively.

EXAMPLE 3

By reaction of the acid from Example 1 with methanol in the presence of p-toluene sulphonic acid, there was otained methyl 3-(2-formyl-3-hydroxy-5-oxocyclopent-1-enyl)propanoate.

EXAMPLE 4

By the method of Example 1 but using 3-[3-acetoxy-5-oxo-2-(β-styryl)-cyclopent-1-enyl]propanoic acid, there was otained 3-(2-formyl-3-acetoxy-5-oxocyclopent-1-enyl)propanoic acid.

EXAMPLE 5

By reaction of the (+) or (−) acids from Example 2 with p-chlorobenzoyl chloride, there were obtained (+)-3-[2-formyl-3-(p-chlorobenzyloxy-5-oxocyclopent1-enyl]propanoic acid and (−)-3-[2-formyl-3-(p-chlorobenzyloxy)-5-oxocyclopent-1-enyl]-propanoic acid respectively.

EXAMPLE 6

By the method of Example 1 but using methyl 3-[3-hydroxy-5-oxo-2-β-styryl)cyclopent-1-enyl]propanoate, there was obtained as an oil methyl 3-(2-formyl-3-hydroxy-5-oxocyclopent-1-enyl)propanoate, λmax (MeOH) 225 nm., I.R. 3440, 1760, 1725 cm.$^{-1}$.

We claim:
1. A compound selected from the group consisting of
1. the carboxylic acid of the formula

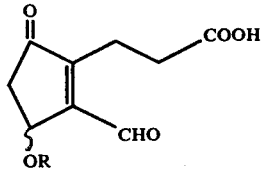

wherein R is hydrogen, $C_{2-4}$ acryl or $C_{2-4}$ haloacyl
2. its alkali metal salt;
3. its $C_{1-4}$ alkyl ester; and
4. its $C_{1-4}$ haloalkyl ester.
2. The carboxylic acid according to claim 1.
3. The sodium or potassium salt according to claim 1.
4. The compound of claim 1, wherein R is selected from the group consisting of acetyl, propionyl, chloroacetyl and 3,3,3-trichloropropionyl.
5. The compound of claim 1, said compound being 3-(2-formyl-3-hydroxy-5-oxocyclopent-1-enyl)-propanoic acid.
6. A pharmaceutical formulation in dosage unit form adapted for administration, comprising per dosage unit an effective amount within the range 1 to 150 mg/kg of animal body weight of a compound of claim 1, admixed with a pharmaceutically acceptable carrier therefor.

* * * * *